(12) United States Patent
Boulton et al.

(10) Patent No.: US 7,375,249 B2
(45) Date of Patent: May 20, 2008

(54) PROCESS FOR THE SYNTHESIS OF ENANTIOMERIC INDANYLAMINE DERIVATIVES

(75) Inventors: Lee Terence Boulton, Cambridge (GB); Ian Campbell Lennon, Cambridge (GB); Eliezer Bahar, Tel Aviv (IL)

(73) Assignee: TEVA Pharmaceutical Industries Ltd., Petach-Tikva (IL)

( * ) Notice: Subject to any disclaimer, the term of this patent is extended or adjusted under 35 U.S.C. 154(b) by 0 days.

(21) Appl. No.: 11/358,995

(22) Filed: Feb. 21, 2006

(65) Prior Publication Data

US 2006/0199974 A1    Sep. 7, 2006

Related U.S. Application Data

(60) Provisional application No. 60/656,362, filed on Feb. 22, 2005.

(51) Int. Cl.
   *C07C 211/00* (2006.01)
(52) U.S. Cl. ...................................... 564/305
(58) Field of Classification Search ................ 564/305
   See application file for complete search history.

(56) References Cited

U.S. PATENT DOCUMENTS

| | | | |
|---|---|---|---|
| 5,532,415 A | | 7/1996 | Youdim et al. |
| 5,703,059 A | * | 12/1997 | Allanson et al. ............... 514/53 |
| 5,936,000 A | | 8/1999 | Romero |
| 6,271,261 B1 | | 8/2001 | Widdowson |
| 6,271,263 B1 | | 8/2001 | Sklarz et al. |
| 6,303,650 B1 | | 10/2001 | Chorev |
| 6,462,222 B1 | | 10/2002 | Chorev |
| 6,538,025 B2 | | 3/2003 | Chorev |
| 6,737,547 B1 | | 5/2004 | Sklarz |
| 2004/0010038 A1 | * | 1/2004 | Blaugrund et al. ......... 514/540 |

FOREIGN PATENT DOCUMENTS

WO    WO 98/27055    6/1998

OTHER PUBLICATIONS

Hus M. L. Davies and Timothy M. Gregg, Asymmetric synthesis of (+)-indatraline using rhodium-catalyzed C-H activation, (2002), Tetrahedron Letters, 43, p. 4951-4953.*

Cossy, J. et al., "Synthesis of Indatraline Using a Suzuki Cross-Coupling Reaction and a Chemoselective Hydrogenation: A Versatile Approach," *Synlett*, vol. 10, pp. 1515-1517 (2003).

Liu et al., Org. Lett., vol. 6, 2004, *Efficient Heterogeneous Asymmetric Transfer Hydrogenation of Ketones Using Highly Recyclable and Accessible Silica-immobilized Ru-TsDPEN Catalysts*; www.paper.edu.cn; © 2004 American Cancer Society, 4 pages.

Oshiro et al., J. Med. Chem. 1991, 34, 2004-2013, *Novel Cerebroprotective Agents with Central Nervous System Stimulating Activity. I. Systhesis and Pharmacology of 1-Amino-7-hydroxyindan Derivatives*; © 1991 American Cancer Society.

* cited by examiner

*Primary Examiner*—Yvonne Eyler
*Assistant Examiner*—Jennifer Y Cho
(74) *Attorney, Agent, or Firm*—Merchant & Gould PC

(57) ABSTRACT

A process for manufacturing (R)-propynylaminoindans, and alternatively, a process for manufacturing (S)-propynylaminoindans. The chiral propynylaminoindans include alkoxy or alkylcarbamates derivatives. The process comprises transfer or pressure hydrogenation in the presence of an optically active catalyst to reduce 1-indanones. The chiral product, either (S)- or (R)-indanols undergo nucleophilic substitution to produce the named product. In an additional aspect, the invention relates to novel intermediates and compounds, namely, substituted indanones, substituted (S)-indanols and substituted (R)-indanols.

24 Claims, 2 Drawing Sheets

Figure 1

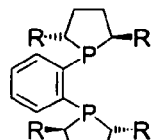
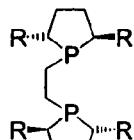
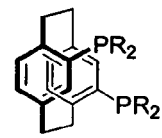

DuPhos　　　　　　　BPE　　　　　　　　PhanePhos

| | | |
|---|---|---|
| R = Me　(R)-MeDuPhos | R = Me　(R)-MeBPE | R = Ph　　　　　　　(R)-PhanePhos |
| R = Et　(R)-EtDuPhos | R = Et　(R)-EtBPE | R = 3,5-Me$_2$Ph　　(R)-XylPhanePhos |
| R = iPr　(S)-iPrDuPhos | R = iPr　(S)-iPrBPE | R = 4-MeO-3,5-Me$_2$Ph　(R)-MeOXylPhanePhos |
| | R = Ph　(S)-PhBPE | R = iPr　　　　　　(R)-iPrPhanePhos |

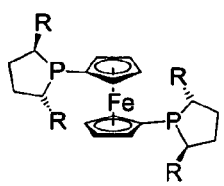
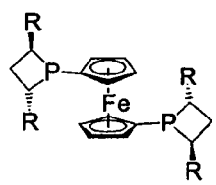
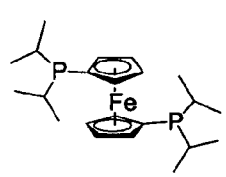

FerroLANE　　　　　　　FerroTANE　　　　　　　DiPFc

| | | |
|---|---|---|
| R = Me　(R)-MeFerroLANE | R = Me　(R)-MeFerroTANE | |
| R = Et　(R)-EtFerroLANE | R = Et　(R)-EtFerroTANE | |
| R = iPr　(S)-iPrFerroLANE | R = Pr　(R)-nPrFerroTANE | |
| | R = iPr　(S)-iPrFerroTANE | |
| | R = tBu　(S)-tBuFerroTANE | |

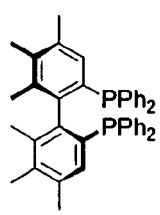
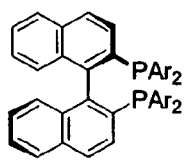
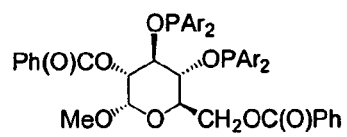

(S)-HexaPHEMP　　　　　　BINAP　　　　　　　　CarboPhos

Ar = Ph　　　(R)-BINAP
Ar = 4MeC$_6$H$_4$　(R)-TolBINAP

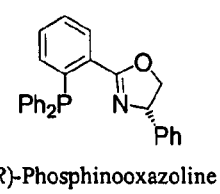
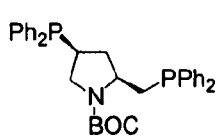
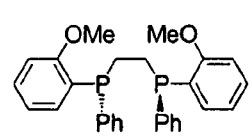

(R)-Phosphinooxazoline　　　(S,S)-BPPM　　　　　　(R,R)-DiPAMP

Figure 2
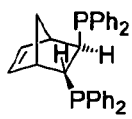
(2R,3R)-Norphos
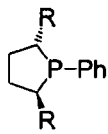
Ph-Phospholane
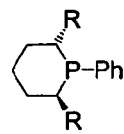
Ph-Phosphinane
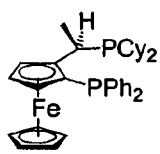
(R)-(S)-Josiphos
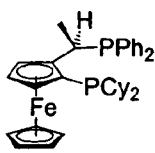
(R)-(S)-Josiphos(A)
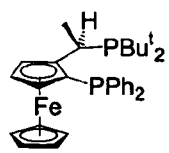
(R)-(S)-Josiphos(B)
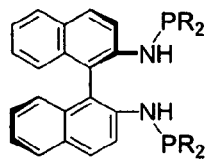
R = Ph  (R)-DPP BINAM
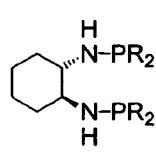
R = Ph  (S)-DPP DACH
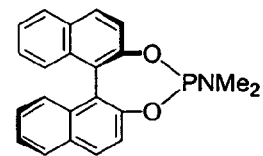
(R)-MonoPHOS
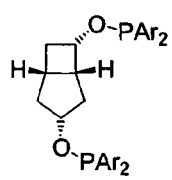
(1R,3R,5R,6S)-Bicyclo[3.2.0]heptane-3,6-diarylphosphinite
BCHD
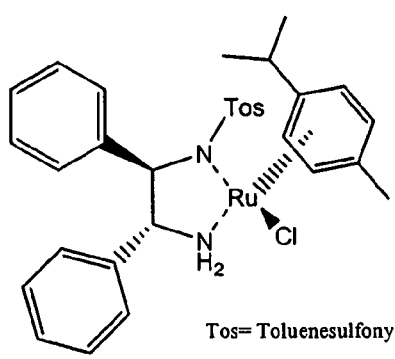
Tos= Toluenesulfonyl
R,R-TSDPEN (Ru) (p-cymene) Cl

US 7,375,249 B2

PROCESS FOR THE SYNTHESIS OF ENANTIOMERIC INDANYLAMINE DERIVATIVES

FIELD OF INVENTION

This invention relates to processes for preparation of indanylamine derivatives.

BACKGROUND OF THE INVENTION

U.S. Pat. No. 5,532,415 discloses R(+)-N-propargyl-1-aminoindan (R(+)PAI), its preparation, and various pharmaceutically acceptable salts thereof. R(+)PAI and salts thereof have been shown to be selective inhibitors of MAO-B, useful in treating Parkinson's disease and various other conditions.

Indanylamine and aminotetralin derivative compounds, such as those of Formula I below, are useful to treat depression, Attention Deficit Disorder (ADD), Attention Deficit and Hyperactivity Disorder (ADHD), Tourett's Syndrome, Alzheimer's Disease and other dementias as described in PCT application publication WO98/27055. The indanylamine derivatives disclosed have been shown to have biological effects in animal models of neurological disease.

Formula I is:

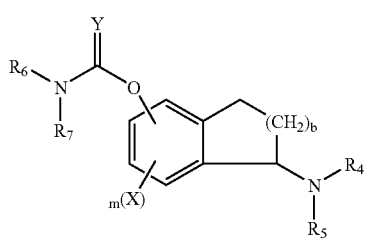

wherein b is 1 or 2; m is from 0-3, Y is O or S, X is halo, $R_4$ is hydrogen or $C_{1-4}$ alkyl, $R_5$ is hydrogen, $C_{1-4}$ alkyl, or optionally substituted propargyl and $R_6$ and $R_7$ are each independently hydrogen, $C_{1-8}$ alkyl, $C_{6-12}$ aryl, $C_{6-12}$ aralkyl, each optionally halo substituted.

One compound disclosed in the PCT application publication is (R)-6-(N-methyl, N-ethyl-carbamoyloxy)-N'-propargyl-1-aminoindan, also known as (3R)-3-(prop-2-ynylamino)-2,3,-dihydro-1H-inden-5-yl ethylmethylcarbamate. Salts thereof are also disclosed, including a ½ L-tartrate salt. This salt has been given the nonproprietary name ladostigil tartrate. Its CAS registry number is 209394-46-7.

PCT application publication WO98/27055 also discloses methods for the preparation of indanylamine and aminotetralin derivatives of Formula I using, for example, as starting materials 3-amino-indan-5-ol or 6-methoxy-indan-1-ylamine. Methods of preparation of the starting materials are also disclosed. 6-Methoxy-indan-1-ylamine is prepared by conversion of 6-methoxy-indan-1-one to 6-methoxy-indan-1-one oxime followed by reduction to 6-methoxy-indan-1-ylamine. Alternatively 6-methoxy-1-aminoindan can be prepared by reductive amination ($NaCNBH_3$ and $NH_4OAc$) of 6-methoxy-indan-1-one to 6-methoxy-indan-1-ylamine. 3-Amino-indan-5-ol can be prepared by using a Friedel-Crafts acylation of an N-protected 3-aminoindan, followed by a Baeyer-Villiger oxidation with subsequent hydrolysis.

These methods for producing starting materials such as 3-amino-indan-5-ol and 6-methoxy-indan-1-ylamine are accompanied by low yields. Thus, there is a need for reliable processes to produce indanylamine and aminotetralin derivatives in high yields as intermediates to prepare aminoindan derivatives and specifically compounds of Formula I, wherein the processes are suitable for industrial production.

Additionally, there is a need for efficient ways of producing enantiomerically enriched indanylamine derivatives. The prior art does not disclose sufficiently efficient methods of enantiomeric purification. In the prior art method of optical resolution of either the starting material or of the end product via diastereomeric salt formation, the undesired enantiomer is "wasted," and the yield is thereby decreased. Another method disclosed in the prior art, resolution using a chiral chromatographic column, is not feasible for a large scale synthesis.

Small scale asymmetric reduction of 1-indanone by transfer hydrogenation using silica-immobilized Ru-TsDPEN catalysts is described by Liu et al. Org. Lett., Vol. 6, 2004, *Efficient Heterogeneous Asymmetric Transfer Hydrogenation of Ketones Using Highly Recyclable and Accessible Silica-immobilized Ru-TsDPEN Catalysts.*

SUMMARY OF THE INVENTION

The present invention relates to a process for manufacturing a compound of the formula:

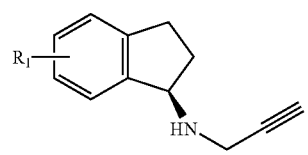

wherein $R_1$ is H, $-OR_2$, or

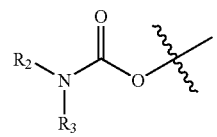

wherein $R_2$ is $C_1$-$C_4$ alkyl, and $R_3$ is H or $C_1$-$C_4$ alkyl.

In an embodiment, the first step of the process of the present invention 1-indanones are reduced by transfer or pressure hydrogenation in the presence of an optically active catalyst and a hydrogen donor to preferentially produce an (S)-indanol. The optically active catalyst comprises a transition metal, such as Ru, and one or more optically active ligands. In the next step, activation of an (S)-indanol at the carbon in the —OH substituted benzylic position, by converting the —OH to a leaving group for subsequent reaction with a nucleophile, such as propargylamine, results in aminoindan derivatives of Formula V.

The present invention additionally relates to a process for manufacturing a compound of the formula:

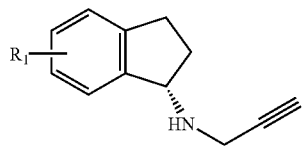

(VII)

wherein $R_1$, $R_2$, and $R_3$ are as defined above.

In an additional embodiment, the first step of the process of the present invention 1-indanones are reduced by transfer or pressure hydrogenation in the presence of an optically active catalyst and a hydrogen donor to preferentially produce an (R)-indanol. The optically active catalyst comprises a transition metal, such as Ru, and one or more optically active ligands. In the next step, activation of an (R)-indanol at the carbon in the —OH substituted benzylic position, by converting the —OH to a leaving group for subsequent reaction with a nucleophile, such as propargylamine, results in (S)-aminoindan derivatives of Formula VII.

In a another aspect, the invention relates to novel intermediates, namely, substituted indanones, and substituted (S)-indanols and substituted (R)-indanols. Both the improved process and novel intermediates are useful in the preparation of therapeutically active compounds used for the treatment of disorders of the central nervous system such as those described above.

DESCRIPTION OF THE FIGURES

FIGS. 1 and 2 illustrate structural formulas of various ligands and catalysts for use in the instant invention.

DETAILED DESCRIPTION OF THE INVENTION

The processes of the present invention produce chiral indanylamine derivatives from readily available, pro-chiral starting materials. The processes of the present invention require few steps and are industrially applicable on a large scale. One advantage of the processes of the present invention is no need to "waste" starting material by diastereomeric salt formation. In addition, the processes do not require large amount of solvents as required in chromatographic separations. The compounds produced by the processes of the current invention are suitable for use as pharmaceuticals, or starting materials or intermediates in the production of a variety of pharmaceuticals, for example those presented in Formula I above.

In various embodiments, halo includes fluoro, chloro, bromo, or iodo. Halides comprise halo groups, such as fluoro, chloro, bromo, or iodo. Alkyl, alkoxy, etc., include both straight and branched groups; but reference to an individual radical such as "propyl" embraces only the straight chain radical, a branched chain isomer such as "isopropyl" being specifically referred to.

"Alkyl" includes linear alkyls, branched alkyls, and cycloalkyls. Additionally, the alkyls may be substituted with alkoxy, halo, and like substitutents. In some embodiments, alkyl is a $C_{1-10}$alkyl, in other embodiments, alkyl is a $C_{1-4}$alkyl. Example alkyl groups include: $C_{1-4}$alkyl, such as methyl, ethyl, propyl, isopropyl, butyl, iso-butyl, sec-butyl, tert-butyl; $C_{1-10}$alkyl, such as methyl, ethyl, propyl, isopropyl, butyl, iso-butyl, sec-butyl, tert-butyl, pentyl, 3-pentyl, hexyl, heptyl, octyl, nonyl and decyl; $(C_{3-12})$cycloalkyl such as cyclopropyl, cyclobutyl, cyclopentyl, cyclohexyl, cycloheptyl, cyclooctyl, bicyclic, or multi-cyclic substituents, such as of the formulas

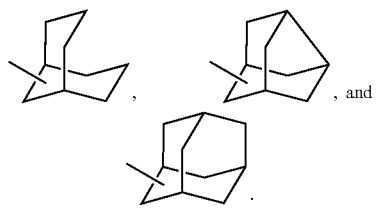

"Alkoxy" includes —O-alkyl in which the alkyl is as described above. Example alkoxys include, but are not limited to: methoxy, ethoxy, n-propoxy, n-butoxy, n-pentoxy, hexyloxy, and heptyloxy.

"Acyl" includes —C(═O)R, for example, —C(═O)H, —C(═O)alkyl, - and C(═O)halo, in which the alkyl is as described above. Specific examples of —C(═O)alkyl include, but are not limited to: acetyl, propanoyl, butanoyl, pentanoyl, 4-methylpentanoyl, hexanoyl, or heptanoyl.

"Aryl" includes a phenyl radical or an ortho-fused bicyclic carbocyclic radical having about nine to twenty ring atoms in which at least one ring is aromatic. Aryl (Ar) can include substituted aryls, such as a phenyl radical having from 1 to 5 substituents, for example, alkyl, alkoxy, halo, and like substituents. In some embodiments, aryl is a $C_{6-18}$ aryl which is either unsubstituted or substituted. Example aryls include, but are not limited to: phenyl, naphthyl, anthracenyl, phenanthrenyl, fluorenyl, tetrahydronaphthyl, or indanyl.

"Alkylaryl" includes an alkyl-aryl wherein the alkyl and the aryl are as described above. Example alkylaryls include, but are not limited to: benzyl, 2-phenethyl and naphthylenemethyl.

The carbon atom content of various hydrocarbon-containing moieties is indicated by a prefix designating a lower and upper number of carbon atoms in the moiety, i.e., the prefix $C_{i-j}$ indicates a moiety of the integer "i" to the integer "j" carbon atoms, inclusive. Thus, for example, $(C_1-C_{10})$alkyl or $C_{1-10}$alkyl refers to alkyl of one to ten carbon atoms, inclusive, and $(C_1-C_4)$alkyl or $C_{1-4}$alkyl refers to alkyl of one to four carbon atoms, inclusive.

The compounds of the present disclosure are generally named according to the IUPAC nomenclature system. Abbreviations, which are well known to one of ordinary skill in the art, may be used (e.g., "Ph" for phenyl, "Me" for methyl, "Et" for ethyl, "h" for hour or hours, "g" or "gm" for gram(s), "mL" for milliliters, and "rt" for room temperature).

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

The indefinite article "a" or "an" and its corresponding definite article "the" as used herein means at least one, or one or more, unless specified otherwise.

The enantiopurity of a product can be expressed in the form of % enantiomeric excess (% e.e.) which is calculated as follows, wherein "maj" is the relative quantity of the major enantiomer and "min" is the relative quantity of the minor enantiomer.

$$\% \text{ e.e.} = \frac{\text{maj} - \text{min}}{\text{maj} + \text{min}} \times 100$$

Specific and preferred values listed below for radicals, substituents, and ranges, are for illustration only; they do not exclude other defined values or other values within defined ranges for the radicals and substituents. The compounds of the disclosure include compounds of formulas (II through V) and like compounds having any combination of the values, specific values, more specific values, and preferred values described herein.

One process of the present invention is represented schematically below. The process of the invention can be divided into multiple steps: (1) hydrogenation of a 1-indanone or derivative thereof in the presence of an optically active catalyst into the corresponding (S)-indanol; and (2) derivatization of the hydroxyl moiety of the indanol into a suitable leaving group (3) thereby facilitating an S$_N$2 substitution at the benzylic carbon by propylgarylamine.

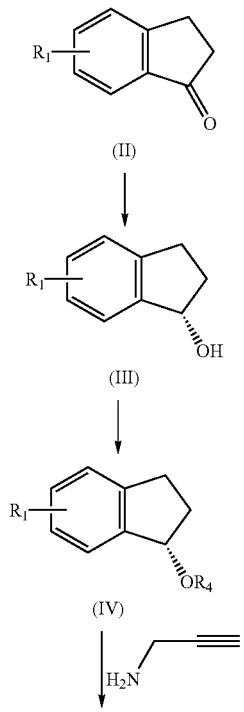

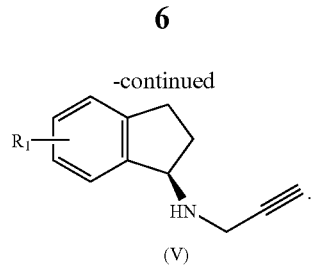

In additional embodiments, the method of the present invention produces (R)-indanol intermediates (VI) and (S)-indanylamine derivatives, including derivatives illustrated by formula VII below.

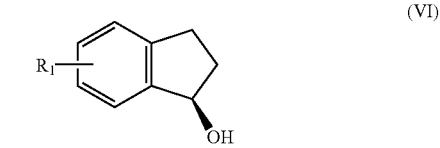

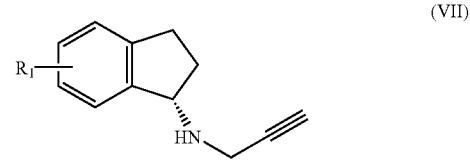

In formulas II through VII, $R_1$ is H, —$OR_2$, or

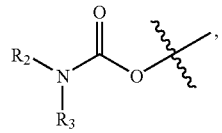

wherein $R_2$ is $C_1$-$C_4$ alkyl, and $R_3$ is H or $C_1$-$C_4$ alkyl, and $R_4$ is a sulphonate ester or halide. In an embodiment, $R_1$ is H. In an another embodiment, $R_1$ is —O(C=O)N$R_2R_3$, wherein $R_2$ is methyl and $R_3$ is ethyl. In a further embodiment, $R_2$ and $R_3$ are methyl.

The first step of the improved process relates to reduction of an indanone in the presence of an optically active catalyst and a hydrogen donor in an appropriate solvent. In some embodiments, the indanone is a compound of Formula II, wherein $R_1$, $R_2$ and $R_3$ are as defined above.

In an embodiment, the indanone is reduced by transfer hydrogenation. Transfer hydrogenation within the context of the present invention, is a process in which a double bond, for instance, a double bond between carbon and oxygen, is hydrogenated in the presence of an organic molecule, a hydrogen donor, other than hydrogen gas, and in the presence of a catalyst. The reactants are combined in a suitable solvent, such as an organic aprotic solvent. An optically active catalyst is used to attain enantiomeric selectivity in the transfer hydrogenation reaction. The nature of the enantiomeric selectivity is affected by the optically active catalyst used. See Table 1. In an embodiment, the hydrogenation is carried out in the presence of an azeotrope comprising a hydrogen donor and an organic base, such as triethylamine. In an embodiment, the transfer hydrogenation is carried out in the presence of a formic acid-triethylamine azeotrope.

A hydrogen donor is a molecule which acts to reduce a double bond by donating hydrogen atoms to the reduced molecule. Hydrogen donors suitable for use the process of transfer hydrogenation include organic acids and salts thereof. Hydrogen donors which are suitable for use in transfer hydrogenation include, but are not limited to: formic acid, ammonium formate, isopropanol, cyclohexene, and 1,3-cyclohexadiene.

Within the context of the invention, an organic aprotic solvent is an organic solvent which does not act as a proton donor or acceptor. Examples of aprotic organic solvents include, but are not limited to, acetonitrile, dichloromethane, toluene, and alkyl ethers. In an embodiment, the organic aprotic solvent is dichloromethane.

In an alternative embodiment, the indanone is reduced by pressure hydrogenation. Pressure hydrogenation is a process in which a double bond, for instance, a double bond between carbon and oxygen, is hydrogenated in the presence of hydrogen gas as a hydrogen donor, and in the presence of a catalyst. An optically active catalyst is used to attain enantiomeric selectivity in the pressure hydrogenation reaction.

The reaction is performed under hydrogen gas at a pressure of between 0.1 to 15 bars (10 to 1500 kPa), under a temperature range of between 10 to 80° C., for a period of time in the range of 1 to 24 hours. In an embodiment, is performed under hydrogen gas at a pressure of about 8 to 12 bars (800 to 1200 kPa). In some embodiments, the reaction temperature is maintained within a range of between about 30-40° C. In one embodiment, the reaction is performed under hydrogen gas pressure of about 10 bars (1000 kPa), at a temperature of about 40° C., and for about 18 hours.

An advantage of catalytic transfer hydrogenation and catalytic pressure hydrogenation is the requirement for small amounts of catalysts. The effective amount of catalyst may be an amount from 1:100 to 1:1000 ratio of catalyst (mol) to starting indanone (mol). In one embodiment, the amount of optically active catalyst is about 1:100 to about 1:250 mol/mol in relation to the indanone starting material.

Within the context of the present invention, an optically active catalyst is used with either transfer hydrogenation or pressure hydrogenation. An optically active catalyst is a catalyst which transforms an achiral center, for instance, a double bond between carbon and oxygen to a chiral center, and in proper reaction conditions, the outcome is a single enantiomer, or a mixture of enantiomers in which one of the enantiomers is in excess. Structures and names of some suitable optically active ligands and catalysts can be seen in FIGS. 1 and 2. Optically active catalysts generally include transition metals complexed to one or more chiral ligands. Examples of suitable transition metals include Ru, Rh, and Ir. In an embodiment, the optically active catalyst comprises Ru.

Within the context of this invention, the term "catalyst" can also refer to a pre-catalyst. A pre-catalyst is a molecule, or complex, in a stable form which is not an active catalyst before being added to the reaction mixture, but becomes an active catalyst under specific conditions within the reaction mixture.

Examples of optically active catalysts or precatalysts suitable for use in the methods of the present invention include, but are not limited to [(R)-HexaPHEMP RuCl₂ (R,R)-DACH], [(R)-HexaPHEMP RuCl₂ (R,R)-DPEN], [(R)-PhanePhos RuCl₂ (S,S)-DACH], [(S)-PhanePhos RuCl₂ (R,R)-DPEN], [(S)-MeO-Xylyl-PhanePhos RuCl₂ (R,R)-DPEN], [(R)-MeO-Xylyl-PhanePhos RuCl₂ (S,S)-DACH], [(S)-SynPhos RuCl₂ (S,S)-DPEN], [(S)-Xylyl-BINAP RuCl₂ (S,S)-DPEN], [(S)-F-Phenyl-PhanePhos RuCl₂ (R,R)-DPEN], [(S)-MeO-Phenyl-PhanePhos RuCl₂ (R,R)-DPEN], [(s)-MeO-Phenyl-PhanePhos RuCl₂ (R,R)-DACH], [(R,R)-Me-DuPhos RuCl₂ (R,R)-DPEN], [(R)-BINAP RuCl₂ (R)-DAIPEN], [(R,R)-Et-DuPhos RuCl₂ (R,R)-DACH], [R,R-TsDPEN (Ru) (p-cymene) Cl], and [S,S-TsDPEN (Ru) (p-cymene) Cl]. In an embodiment, the method of the present invention comprises S,S-TsDPEN (Ru) (p-cymene) Cl as an optically active catalyst.

In a second step, either (S)- or (R)-indanol is activated at the —OH substituted benzylic carbon for nucleophilic substitution. In an embodiment, the hydroxyl moiety is derivatized to form a suitable leaving group for nucleophilic substitution. In an embodiment, the nucleophilic substitution is S$_N$2. The second step is based on methods of nucleophilic substitution described in the literature, in an appropriate solvent. (See March's Advanced Organic Chemistry; Michael B. Smith and Jerry March, 5$^{th}$ edition, Chapter 10.) In an embodiment, the nucleophile is propargylamine.

Within the context of the invention, a leaving group is an atom (or a group of atoms) with electron withdrawing ability that is displaced as a stable species, taking with it the bonding electrons. In an embodiment, the leaving group will facilitate an S$_N$2 reaction between the substituted benzylic carbon and the propargylamine. Examples of suitable leaving groups include sulfonate esters and halides. In an embodiment, the leaving group is methane sulfonate ester.

The process of the present invention may further comprise the conversion of a product into a pharmaceutically acceptable salt. In the practice of this invention, pharmaceutically acceptable salts include, but are not limited to, the mesylate, maleate, fumarate, tartrate, hydrochloride, hydrobromide, esylate, p-toluenesulfonate, benzoate, acetate, phosphate and sulfate salts. The present invention additionally comprises products as pharmaceutically acceptable salts.

EXAMPLES

Suitable indanone starting materials and other materials described are commercially available. Derivatization of indanone starting materials, such as 6-hydroxy-1-indanone, to form substituted starting materials for use in the processes of the present invention is described below.

Example 1

Dimethyl-carbamic acid 3-oxo-indan-5-yl ester

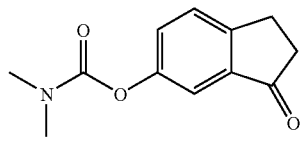

Dimethyl carbamyl chloride (7.7 mL, 83.3 mmol) was added dropwise to a stirred suspension of 6-hydroxy-1-indanone (10.290 g, 69.4 mmol) and potassium carbonate (12.48 g, 90.3 mmol) in DMF (50 mL) at 0° C. (external) over a period of 30 minutes. One hour after the addition was complete the cold bath was removed and the reaction was allowed to warm slowly to room temperature over 2 hours. The reaction mixture was diluted with methyl tert-butyl ether (50 mL) and water (100 mL) and the resultant solid was collected by filtration and washed with water (50 mL) and then methyl tert-butyl ether (50 mL). The collected material was dried under vacuum overnight. The crude product was purified by solvent slurry in methyl tert-butyl ether (50 mL) before being collected by filtration, washed with additional methyl tert-butyl ether (20 mL) and dried to afford the title compound (16) (14.877 g, 98%). 1H NMR (400 MHz, CDCl3) δ ppm 7.47-7.45 (2H, m, Ar), 7.36 (1H, dd, J 8 and 2, Ar), 3.14-3.11 [5H, m, OCCH2 and Me, incl. at 3.11 (3H, s, Me)], 3.02 (3H, s, Me) and 2.74-2.71 (2H, m, OCCH2CH2).

Example 2

Dimethyl-carbamic acid 3-hydroxy-indan-5-yl ester

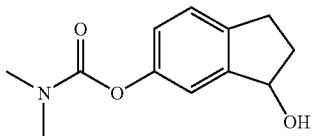

Example 2a

Transfer Hydrogenation

Formic acid (4.3 mL, 114.0 mmol) was added dropwise to a stirred solution of dimethyl-carbamic acid 3-oxo-indan-5-yl ester (5.00 g, 22.8 mmol), (R,R)-TsDPEN Ru (p-cymene)Cl (58 mg, 0.1 mmol) and triethylamine (15.9 mL, 114.0 mmol) in dichloromethane (21 mL) at 35° C. (external) over a period of 50 minutes. After 20 hours, additional (R,R)-TsDPEN Ru (p-cymene)Cl (58 mg, 0.1 mmol) formic acid (0.9 mL, 22.8 mmol) and triethylamine (3.2 mL, 22.8 mmol) were added to the reaction and heating was continued for 19 hours. The reaction was allowed to cool before being poured into saturated aqueous sodium hydrogen carbonate solution (150 mL) and was extracted with dichloromethane (150 mL+100 mL). The organic material was dried (MgSO$_4$), filtered and concentrated under reduced pressure to afford the R-enantiomer of the title compound (5.144 g, quant.). Analysis of this material by chiral LC indicated it to be 98% e.e.

Example 2b

Pressure Hydrogenation

[(R,R)-Me-DuPhos RuCl$_2$ (R,R)-DPEN] (1.7 mg, 0.002 mmol) and dimethyl-carbamic acid 3-oxo-indan-5-yl ester (110 mg, 0.5 mmol) were placed in a glass liner within an Argonaut Endeavor pressure vessel. The vessel was assembled. The vessel was pressurised to 10 bar with nitrogen and the pressure was released. This was repeated a further two times. A solution of potassium tert-butoxide [3 ml (of a solution of commercial 0.25 ml of 1.0 M potassium tert-butoxide solution in tert-butanol made up to 30 ml with dry degassed 2-propanol), 0.025 mmol)] was added to the vessel. The vessel was pressurised to 10 bar with nitrogen and the pressure was released. This was repeated one more time. The vessel was heated to 40° C. (internal) with stirring before being pressurised to 10 bar with hydrogen. After 18 hours, the vessel was allowed to cool to room temperature before being vented and the reaction solution concentrated under reduced pressure to afford the R-enantiomer of title compound. $^1$H NMR (400 MHz, CDCl$_3$) δ ppm 7.20 (1H, d, J 9, Ar), 7.14 (1H, d, J 3, Ar), 6.98 (1H, dd, J 8 and 2, Ar), 5.20 (1H, dd, J 6 and 6, CHOH), 3.10 (3H, s, Me), 3.04-2.97 [4H, m, OCHCH$_2$CHH and Me, incl. at 3.01 (3H, s, Me)], 2.83-2.72 (1H, m, OCHCH$_2$CHH), 2.59-2.49 (1H, m, OCHCHH), 1.99-1.91 (1H, m, OCHCHH) and 1.84 (1H, brs, OH). Analysis of this material by chiral LC indicated it to be 73% e.e.

Similar procedures were performed using pre-catalysts as listed below in Table 1. The conversion percent enantiomeric excess percent are listed in the table for each example.

TABLE 1

| | | | |
|---|---|---|---|
| 1 | [(S)-Xylyl-HexaPHEMP RuCl$_2$ (S,S)-DPEN] | >95 | 30 (S) |
| 2 | [(R)-HexaPHEMP RuCl$_2$ (R,R)-DACH] | >95 | 26 (R) |
| 3 | [(R)-HexaPHEMP RuCl$_2$ (R,R)-DPEN] | >95 | 35 (R) |
| 4 | [(R)-PhanePhos RuCl$_2$ (S,S)-DACH] | >95 | 16 (S) |
| 5 | [(S)-PhanePhos RuCl$_2$ (R,R)-DPEN] | >95 | 37 (R) |
| 6 | [(S)-MeO-Xylyl-PhanePhos RuCl$_2$ (R,R)-DPEN] | >95 | rac |
| 7 | [(R)-MeO-Xylyl-PhanePhos RuCl$_2$ (S,S)-DACH] | >95 | 62 (S) |
| 8 | [(S)-Tol-BINAP RuCl$_2$ (S,S)-DPEN] | >95 | 28 (S) |
| 9 | [(S)-SynPhos RuCl$_2$ (S,S)-DPEN] | >95 | 35 (S) |
| 10 | [(S)-Xylyl-BINAP RuCl$_2$ (S,S)-DPEN] | >95 | 38 (S) |
| 11 | [(S)-F-Phenyl-PhanePhos RuCl$_2$ (R,R)-DPEN] | >95 | 49 (R) |
| 12 | [(S)-MeO-Phenyl-PhanePhos RuCl$_2$ (R,R)-DPEN] | >95 | 35 (R) |
| 13 | [(S)-MeO-Phenyl-PhanePhos RuCl$_2$ (R,R)-DACH] | >95 | 23 (R) |
| 14 | [(S)-Xylyl-PhanePhos RuCl$_2$ (R,R)-DPEN] | >95 | 62 (R) |
| 15 | [(R,R)-Me-DuPhos RuCl$_2$ (R,R)-DPEN] | >95 | 73 (R) |
| 16 | [(R)-BINAP RuCl$_2$ (R)-DAIPEN] | >95 | 30 (R) |
| 17 | [(R,R)-Et-DuPhos RuCl$_2$ (R,R)-DACH] | >95 | 27 (R) |

† Conversion estimated from the $^1$H NMR of the crude material.
‡ Enantiomeric excess was determined by chiral LC analysis. Configuration was assigned by comparison with the ethylmethyl analog.

Comparative Example 2c

Racemic Form

Sodium borohydride (66 mg, 1.7 mmol) was added to a stirred suspension of dimethyl-carbamic acid 3-oxo-indan-5-yl ester (381 mg, 1.7 mmol) in a mixture for THF (5 mL) and water (0.5 mL) at 0° C. (external). After stirring at this temperature for 2 hour, saturated aqueous ammonium chloride solution (10 mL) and ethyl acetate (20 mL) was added. The organic layer was dried (MgSO$_4$), filtered and concentrated under reduced pressure to afford a racemic mixture of the title compound (343 mg, 89%.). $^1$H NMR (400 MHz, CDCl$_3$) δ ppm 7.20 (1H, d, J 9, Ar), 7.14 (1H, d, J 3, Ar), 6.98 (1H, dd, J 8 and 2, Ar), 5.20 (1H, dd, J 6 and 6, CHOH), 3.10 (3H, s, Me), 3.04-2.97 [4H, m, OCHCH$_2$CHH and Me, incl. at 3.01 (3H, s, Me)], 2.83-2.72 (1H, m, OCHCH$_2$CHH), 2.59-2.49 (1H, m, OCHCHH), 1.99-1.91 (1H, m, OCHCHH) and 1.84 (1H, brs, OH).

Example 3

Ethylmethyl-carbamic acid 3-oxo-indan-5-yl ester

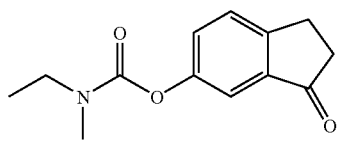

Ethylmethyl carbamyl chloride (15.5 g, 127.57 mmol) was added to a stirred suspension of 6-hydroxy-1-indanone (17.2 g, 116.1 mmol) and potassium carbonate (31.8 g, 188 mmol) in acetonitrile (800 mL) at room temperature over a period of 15 minutes. The reaction mixture was heated to reflux and refluxed for 18 hours. The reaction mixture was cooled to ambient temperature, the solvent evaporated and the residue was diluted with water (250 mL) and extracted three times with toluene (250 mL). The combined organic phase was dried on MgSO$_4$ and toluene was evaporated in a rotary evaporator. The crude crystalline product was purified by crystallization from 2-propanol (200 mL), collected by filtration, and dried under vacuum at 50° C. to afford the title compound (22 g, 81.5%). $^1$H NMR (300 MHz, CDCl$_3$) δ ppm 7.47-7.44 (2H, m, Ar), 7.36 (1H, dd, J 8.4 and 2.1, Ar), 3.52-3.37 (2H, m, NCH$_2$CH$_3$), 3.14-3.108 [2H, m, OCCH$_2$CH$_2$ and incl. NCH$_3$ (two rotamers), at 3.08 and 2.99 (3H, s, Me)], 2.74-2.71 (2H, m, OCCH$_2$CH$_2$) and 1.25 and 1.19 (two rotamers) (3H,two triplets, J 6.9). Mass Spectrum (FAB+) [MH$^+$]=234

Example 4

Ethyl-methyl-carbamic acid 3-hydroxy-indan-5yl ester

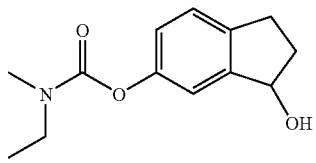

Example 4a

Transfer Hydrogenation

Formic acid (6.7 mL, 178.6 mmol) was added dropwise to a stirred solution of ethyl-methyl-carbamic acid 3-oxo-indan-5-yl ester (8.33 g, 35.7 mmol), (R,R)-TsDPEN Ru (p-cymene)Cl (114 mg, 0.2 mmol) and triethylamine (24.9 mL, 178.6 mmol) in dichloromethane (31 mL) at 35° C. (external) over a period of 30 minutes. After 18 hours, additional (R,R)-TsDPEN Ru (p-cymene) Cl (114 mg, 0.2 mmol) formic acid (1.3 mL, 35.7 mmol) and triethylamine (5.0 mL, 35.7 mmol) were added to the reaction and heating was continued for 24 hours. The reaction was allowed to cool before being poured into saturated aqueous sodium hydrogen carbonate solution (200 mL) and was extracted with dichloromethane (200 mL+150 mL). The organic material was washed with brine (100 mL), dried (MgSO$_4$), filtered and concentrated under reduced pressure. The crude material was purified by passage through a pad of silica using methyl tert-butyl ether as eluant to afford the R-enantiomer of the title compound (8.462 g, quant.). Analysis of this material by chiral LC indicated it to be 99% e.e.

Example 4b

Transfer Hydrogenation

The procedure described in example 4a is repeated with (S,S)-TsDPEN Ru (p-cymene)Cl in place of (R,R)-TsDPEN Ru (p-cymene)Cl. The S-enantiomer of the title compound is attained.

Comparative Example 4c

Racemic Form

Sodium borohydride (50 mg, 1.3 mmol) was added to a stirred suspension of ethyl-methyl-carbamic acid 3-oxo-indan-5-yl ester (306 mg, 1.3 mmol) in methanol (5 mL) at room temperature. After stirring at this temperature for 2 hour, saturated aqueous ammonium chloride solution (10 mL), water (10 mL) and ethyl acetate (20 mL) were added. The layers were separated and then the aqueous was extracted with additional ethyl acetate (20 mL). The combined organic layers were dried (MgSO$_4$), filtered and concentrated under reduced pressure to afford a racemic mixture of the title compound (330 mg, quant.). $^1$H NMR (400 MHz, CDCl$_3$) δ ppm 7.20 (1H, d, J 8, Ar), 7.14 (1H, s, Ar), 6.98 (1H, d, J 8, Ar), 5.20 (1H, dd, J 6 and 6, CHOH), 3.47 (rotamer A, 1H, q, J 7, MeCH$_2$N), 3.40 (rotamer B, 1H, q, J 8, MeCH$_2$N), 3.06-2.97 [4H, MeN and OCHCH$_2$CHH, incl. at 3.06 (rotamer A, 1.5H, s, MeN) and 2.99 (rotamer B, 1.5H, s, MeN)], 2.81-2.74 (1H, m, OCHCH$_2$CHH), 2.55-2.47 (1H, m, OCHCHH), 1.99-1.91 (1H, m, OCHCHH), 1.66 (1H, brs, OH), 1.24 (rotamer A, 1.5H, t, J 7, MeCH$_2$N) and 1.19 (rotamer B, 1.5H, t, J 7, MeCH$_2$N).

Example 5

1-Indanol

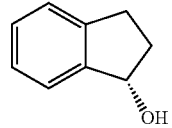

Formic acid (7.2 mL, 190.7 mmol) was added dropwise to a stirred solution of 1-indanone (5.09 g, 38.5 mmol), (S,S)-TsDPEN Ru (p-cymene) Cl (231 mg, 0.36 mmol) and triethylamine (26 mL, 186.5 mmol) in dichloromethane (50 mL) at 30° C. (internal) under a nitrogen atmosphere over a period of 30 minutes. The internal temperature reached 35° C. during the addition. After stirring for 19 hours at 30° C., $^1$H NMR analysis indicated a conversion of 80%. Additional (S,S)-TsDPEN Ru (p-cymene)Cl (47 mg, 0.07 mmol) was added to the reaction mixture followed by formic acid (3 mL, 79.5 mmol) dropwise over 30 minutes. After stirring for 21 hours at 35° C. (internal), $^1$H NMR analysis indicated complete conversion. The reaction was allowed to cool to room temperature before saturated aqueous sodium hydrogen carbonate solution (100 mL) was added. The two layers were separated then the aqueous layer was further extracted with dichloromethane (80 mL). The combined organic layers were washed with water (80 mL), dried (MgSO$_4$), filtered and concentrated under reduced pressure. The crude material was purified by passage trough a pad of silica using methyl tert-butyl ether as eluant to afford the S-enantiomer of the title compound as a red solid. (5.06 g, 98%). $^1$H NMR (400 MHz, d$_6$-DMSO) δ ppm 7.37-7.34 (1H, m, Ar), 7.26-7.19 (3H, m, Ar), 5.23 (1H, d, J 6, OH), 5.06 (1H, dt, J 6 and 6, CH), 2.97-2.90 (1H, m, CHH), 2.77-2.69 (1H, m, CHH), 2.39-2.31 (1H, m, CHH) and 1.84-1.75 (1H, m, CHH). Analysis of this material by chiral GC indicated it to be 98% e.e.

Example 6

(S)-Dimethyl-carbamic acid 3-prop-2-ynylamino-indan-5-yl ester

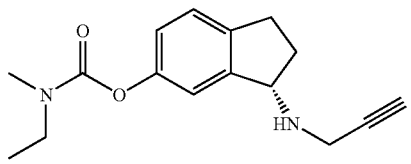

Methanesulfonyl anhydride (296 mg, 1.7 mmol) as a solution in dichloromethane (1.5 mL+0.5 mL) was added to a stirred solution of (R)-dimethyl-methyl-carbamic acid 3-hydroxy-indan-5-yl ester (188 mg, 0.8 mmol, product of example 1a) and triethylamine (0.47 mL, 3.4 mmol) in dichloromethane (2 mL) at −78° C. (external) over 10 minutes. The reaction was maintained at this temperature for 1 hour before propargylamine (1.20 mL, 17.0 mmol) was added. The reaction was allowed to warm slowly to room temperature overnight before being partitioned between ethyl acetate (20 mL) and ice-water (20 mL). The organic material was concentrated under reduced pressure to afford a brown oil which was partitioned between methyl tert-butyl ether (10 mL) and aqueous hydrochloric acid (1M, 10 mL). The aqueous layer was basified by addition of aqueous sodium hydroxide solution (2M, 16 mL) before being extracted with ethyl acetate (10 mL). This final organic extract was dried (MgSO$_4$), filtered and concentrated under reduced pressure to afford the title compound (175 mg, 80%). $^1$H NMR (400 MHz, CDCl$_3$) δ ppm 7.19 (1H, d, J 8, Ar), 7.09 (1H, d, J 2, Ar), 6.94 (1H, dd, J 8 and 2, Ar), 4.39 (1H, dd, J 6 and 6, CHNH), 3.54 (1H, Dd, J 17 and 3, NCHH), 3.49 (1H, Dd, J 16 and 3, HNCHH), 3.09 (3H, s, Me), 3.03-2.96 [4H, m, NCHCHH and Me incl. at 3.00 (3H, s, Me)], 2.83-2.75 (1H, m, NCHCHH), 2.48-2.39 (1H, m, NCHCH$_2$CHH), 2.25 (1H, t, J 2, ≡CH) and 1.92-1.83 (1H, m, NCHCH$_2$CHH). Analysis of this material by chiral LC indicated it to be 70% e.e.

Example 7a (S)-Ethyl-methyl-carbamic acid 3-prop-2-ynylamino-indan-5-yl ester

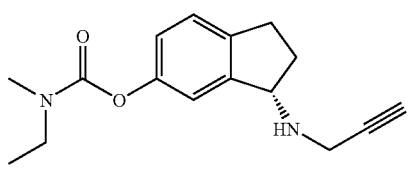

Methanesulfonyl anhydride (1.544 g, 8.9 mmol) as a solution in dichloromethane (7.5 mL+2.5 mL) was added to a stirred solution of (R)-ethyl-methyl-carbamic acid 3-hydroxy-indan-5-yl ester (1.04 g, 4.4 mmol) and triethylamine (2.5 mL, 17.7 mmol) in dichloromethane (10 mL) at −35° C. (external) over 10 minutes. The reaction was maintained at this temperature for 45 minutes before propargylamine (3.0 mL, 44.3 mmol) was added. The reaction was allowed to warm slowly to room temperature overnight before being partitioned between ethyl acetate (100 mL) and ice-water (100 mL). The organic material was concentrated under reduced pressure to afford a brown oil which was partitioned between methyl tert-butyl ether (50 mL) and aqueous hydrochloric acid (1M, 50 mL). The aqueous layer was basified by addition of aqueous sodium hydroxide solution (2M, 40 mL) before being extracted with ethyl acetate (50 mL). This final organic extract was dried (MgSO$_4$), filtered and concentrated under reduced pressure to afford the title compound (842 mg, 70%). $^1$H NMR (400 MHz, CDCl$_3$) δ ppm 7.19 (1H, d, J 8, Ar), 7.09 (1H, s, Ar), 6.94 (1H, brd, J, 8, Ar), 4.39 (1H, dd, J 6 and 6, NHCH), 3.55 (1H, Dd, J 17 and 2, NCHH), 3.49 (1H, Dd, J 17 and 2, NCHH), 3.46 (rotamer A, 1H, q, J 8, MeCHHN), 3.40 (rotamer B, 1H, q, J 7, MeCHHN), 3.06 (rotamer A, 1.5H, s, MeN), 3.03-2.95 [2.5H, m, NCHCH$_2$CHH and rotamer B, Me, incl. at 2.98 (rotamer B, 1.5H, s, MeN)], 2.83-2.75 (1H, m, NCHCH$_2$CHH), 2.48-2.39 (1H, m, NCHCHH), 2.25 (1H, t, J 2, ≡CH), 1.92-1.83 (1H, m, NCHCHH), 1.23 (rotamer A, 1.5H, t, J 7, MeN) and 1.18 (rotamer B, 1.5H, t, J 7, MeN). Analysis of this material by chiral LC indicated it to be 62% e.e.

Example 7b (R)-Ethyl-methyl-carbamic acid 3-prop-2-ynylamino-indan-5-yl ester (ladostigil)

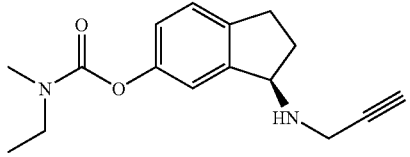

The procedure of example 7a is repeated with (S)-ethyl-methyl-carbamic acid 3-hydroxy-indan-5-yl ester instead of (R)-ethyl-methyl-carbamic acid 3-hydroxy-indan-5-yl ester. The R-enantiomer is produced.

Example 8

N-propargyl-1-(R)aminoindan (Rasagiline)

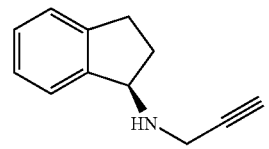

Methanesulfonyl anhydride (3.0 g, 17.2 mmol) as a solution in dichloromethane (8 mL+4 mL) was added to a stirred solution of (S)-1-indanol (1.02 g, 7.6 mmol) and triethylamine (4.4 mL, 31.5 mmol) in dichloromethane (20 mL) at −26° C. (internal, −35° C. external) over 10 minutes. During the addition the internal temperature rose to −20° C. The reaction was maintained at −29° C. (internal, −35° C., external) for 45 minutes before propargylamine (5 mL, 78 mmol) was added over 2 minutes. The reaction was allowed to warm slowly to room temperature overnight before being portioned between ethyl acetate (50 mL) and ice-water (75 mL, pH of solution 9.7). The organic layer was concentrated under reduced pressure to afford a brown oil which was partitioned between methyl tert-butyl ether (50 mL) and aqueous hydrochloric acid (1M, 40 mL, pH of solution <1). The aqueous layer was basified to pH>12.5 by addition of aqueous sodium hydroxide solution (2M, 30 mL) before being extracted with ethyl acetate (50 mL+30 mL). The combined final organic extracts were dried (MgSO$_4$), filtered and concentrated under reduced pressure to afford the title compound as a brown liquid (0.81 g, 68%). Analysis of this material by chiral GC indicated it to be 46% e.e.

Throughout this application various publications, published patent applications, and published patents are referenced. The disclosures of these publications in their entireties are hereby incorporated by reference into this application in order to more fully describe the state of the art to which this invention pertains.

The invention claimed is:

1. A process for manufacturing a compound of the formula:

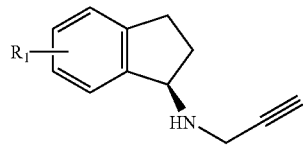

(V)

wherein R$_1$ is H, —OR$_2$, or

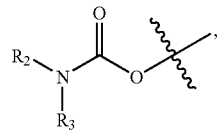

wherein R$_2$ is C$_1$-C$_4$ alkyl, and R$_3$ is H or C$_1$-C$_4$ alkyl, the process comprising:

a. reducing an indanone derivative of the formula:

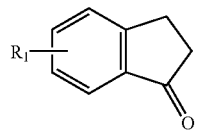

wherein R$_1$ is defined as above, in the presence of an optically active catalyst and a hydrogen donor to form a compound of the formula:

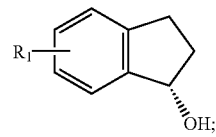

b. activating the carbon in the —OH substituted benzylic position of the product of step a by converting the —OH to a leaving group; and c. reacting the product of step b with

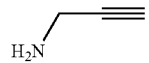

to form the above desired product.

2. The process of claim 1 wherein the reducing of step a is accomplished through transfer hydrogenation or through pressure hydrogenation.

3. The process of claim 2 wherein the hydrogen donor is in the form of hydrogen gas.

4. The process of claim 1 wherein the reducing of step a is accomplished through transfer hydrogenation.

5. The process of claim 1 wherein the optically active catalyst comprises a transition metal complexed to at least one optically active ligand.

6. The process of claim 2 wherein the transition metal is one of a group consisting of: Ru, Rh, and Ir.

7. The process of claim 6 wherein the transition metal is Ru.

8. The process of claim 7 wherein the optically active catalyst is one of the group consisting of: [(R)-HexaPHEMP RuCl$_2$ (R,R)-DACH], [(R)-HexaPHEMP RuCl$_2$ (R,R)-DPEN], [(R)-PhanePhos RuCl$_2$ (S,S)-DACH], [(S)-PhanePhos RuCl$_2$ (R,R)-DPEN], [(S)-MeO-Xylyl-PhanePhos RuCl$_2$ (R,R)-DPEN], [(R)-MeO-Xylyl-PhanePhos RuCl$_2$ (S,S)-DACH], [(S)-SynPhos RuCl$_2$ (S,S)-DPEN], [(S)-Xylyl-BINAP RuCl$_2$ (S,S)-DPEN], [(S)-F-Phenyl-PhanePhos RuCl$_2$ (R,R)-DPEN], [(S)-MeO-Phenyl-PhanePhos RuCl$_2$ (R,R)-DPEN], [(S)-MeO-Phenyl-PhanePhos RuCl$_2$ (R,R)-DACH], [(R,R)-Me-DuPhos RuCl$_2$ (R,R)-DPEN], [(R)-BINAP RuCl$_2$ (R)-DAIPEN], [(R,R)-Et-DuPhos RuCl$_2$ (R,R)-DACH], [R,R-TsDPEN (Ru) (p-cymene) Cl], and [S,S-TsDPEN (Ru) (p-cymene) Cl].

9. The process of claim 8 wherein the optically active catalyst is S,S-TsDPEN (Ru) (p-cymene) Cl.

10. The process of claim 4 wherein step a is performed in the presence of an organic aprotic solvent.

11. The process of claim 10 wherein the organic aprotic solvent is dichloromethane.

12. The process of claim 4 wherein the hydrogen donor is one of the group consisting of formic acid, ammonium formate, and 1,3-cyclohexadiene.

13. The process of claim 12 wherein the hydrogen donor is formic acid.

14. The process of claim 4 wherein the reduction of step a is accomplished in the presence of an azeotrope comprising an organic base and a hydrogen donor.

15. The process of claim 14 wherein the organic base is triethylamine.

16. The process of claim 1 wherein the leaving group is a member of the group consisting of: sulfonate esters, and halides.

17. The process of claim 16 wherein the leaving group is methane sulfonate ester.

18. The process of claim 1 wherein R$_1$ is H.

19. The process of claim 1 wherein R$_1$ is

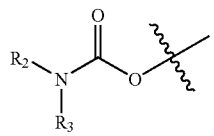

wherein R$_2$ and R$_3$ are as defined above.

20. The process of claim 19 wherein $R_2$ is methyl and $R_3$ is ethyl.

21. The process of claim 20 wherein the indanone derivative of step a is a compound of a formula:

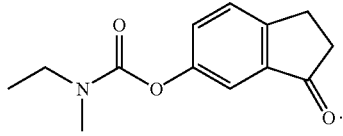

22. A process for manufacturing a compound of the formula:

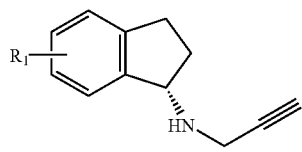
(VII)

wherein $R_1$ is H, —$OR_2$, or

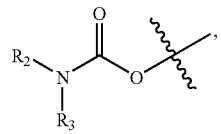

wherein $R_2$ is $C_1$-$C_4$ alkyl, and $R_3$ is H or $C_1$-$C_4$ alkyl, the process comprising:

a. reducing an indanone derivative of the formula:

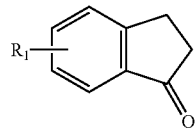

wherein $R_1$ is defined as above, in the presence of an optically active catalyst and a hydrogen donor to form a compound of the formula

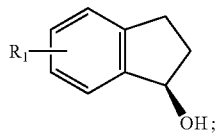

b. activating the carbon in the —OH substituted benzylic position of the product of step a by converting the —OH to a leaving group; and
c. reacting the product of step b with

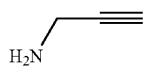

to form the above desired product.

23. A process according to claim 22 further comprising transforming the product of step c into a pharmaceutically acceptable salt.

24. The process of claim 23 wherein the pharmaceutically acceptable salt is the mesylate or tartrate salt.

* * * * *